United States Patent [19]

Tanaka et al.

[11] Patent Number: 5,605,806
[45] Date of Patent: Feb. 25, 1997

[54] REAGENT FOR ASSAYING ENDOTOXIN

[75] Inventors: Shigenori Tanaka; Hiroshi Tamura, both of Tokyo, Japan

[73] Assignee: Seikagaku Kogyo Kabushiki Kaisha (Seikagaku Corporation), Tokyo, Japan

[21] Appl. No.: 427,260

[22] Filed: Apr. 24, 1995

Related U.S. Application Data

[63] Continuation of Ser. No. 847,102, filed as PCT/JP91/01118, Aug. 22, 1991, published as WO92/03736, Mar. 5, 1992, abandoned.

[30] Foreign Application Priority Data

Aug. 22, 1991 [JP] Japan ..................... 2-218954

[51] Int. Cl.⁶ .................. G01N 33/569; G01N 33/543; G01N 33/579
[52] U.S. Cl. .................. 435/7.32; 435/184; 435/962; 436/518; 436/529; 436/530; 436/531; 530/388.2; 530/388.26; 530/389.1
[58] Field of Search ............. 435/7.32, 23, 184, 435/962; 436/518, 529, 530, 531, 69; 530/413, 388.2, 388.26, 389.1

[56] References Cited

U.S. PATENT DOCUMENTS 4,414,336  11/1983  Watanabe et al. ............. 436/502
5,155,032  10/1992  Tanaka et al. ............... 435/18
5,202,253   4/1993  Esmon et al. ............... 530/413
5,266,461  11/1993  Tanaka ..................... 435/7.21

FOREIGN PATENT DOCUMENTS 0291856    11/1988  European Pat. Off. .
58-13516    1/1983  Japan .
59-27828    2/1984  Japan .
60-125565   7/1985  Japan .
1-175945    7/1989  Japan ..................... 435/962
1219562     9/1989  Japan .
1235852     9/1989  Japan .
WO8900446   1/1989  WIPO .

*Primary Examiner*—Christina Y. Chan
*Assistant Examiner*—James L. Grun
*Attorney, Agent, or Firm*—Sughrue, Mion, Zinn, Macpeak & Seas

[57] ABSTRACT

The present invention provides a reagent for assaying an endotoxin which comprises limulus amoebocyte lysate and an antibody to (1 → 3)-β-D-glucan sensitive factor or a reagent which comprises a lysate substantially free from (1 → 3)-β-D-glucan sensitive factor. The reagent of the present invention makes it possible to assay an endotoxin originating from gram-negative bacteria contained in a biological sample such as blood, urine and cerebrospinal fluid at an extremely high sensitivity without being affected by (1 → 3)-β-D-glucan.

11 Claims, 6 Drawing Sheets

REAGENT FOR ASSAYING ENDOTOXIN

This is a Continuation of application Ser. No. 07/847, 102, filed as PCT/JP91/01118 on Aug. 22, 1991 and published as WO92/03736 on Mar. 5, 1992, now abandoned.

FIELD OF THE INVENTION

This invention relates to a reagent for assaying an endotoxin with the use of limulus amebocyte lysate.

BACKGROUND OF THE INVENTION

There has been known a method for assaying an endotoxin with the use of limulus amebocyte lysate (hereinafter referred to simply as lysate) by taking advantage of a fact that said lysate coagulates with a trace amount of an endotoxin. Subsequent biochemical studies have revealed that this coagulation is caused by stepwise activation of several coagulation factors [cf. Takanori Nakamura et al., Japanese Journal of Bacteriology, 38,781–803 (1983)].

When an endotoxin is added to the lysate, as shown in FIG. 1, factor C (an endotoxin-sensitive factor, molecular weight: 123,000) is activated. Then, the activated factor C definitively hydrolyzes and activates factor B (molecular weight: 64,000). The activated factor B thus formed activates proclotting enzyme (molecular weight: 54,000) and thus convert the same into clotting enzyme. The clotting enzyme definitively hydrolyzes specific sites, i.e., $Arg^{18}$-$Thr^{19}$ and $Arg^{46}$-$Gly^{47}$, of coagulogen (a coagulation protein, molecular weight: 19,723) and thus liberates peptide C to thereby convert the coagulogen into coagulin, which causes coagulation (gelation). Iwanaga et al. [Haemostasis, Z, 183–199 (1978)] further proposed a highly quantitative assay method wherein the lysate is combined with a synthetic peptide having an amino acid sequence in common with the above-mentioned hydrolysis sites of coagulogen, namely a chromogenic substrate Boc-Leu-Gly-Arg-p-nitroanilide (pNA) or a fluorogenic substrate Boc-Leu-Gly-Arg-4-methylcoumaryl-7-amide.

This assay method depends on a series of reactions involving a cascade mechanism wherein an endotoxin acts as a trigger so as to successively activate coagulation factors all of which are serine protease precursors and thus the coagulin is formed finally.

When $(1 \to 3)$-$\beta$-D-glucan is added to the lysate, factor G shown in FIG. 1 is activated and the activated factor G thus formed converts the proclotting enzyme into the clotting enzyme. Next, the clotting enzyme converts the coagulogen into the coagulin, similar to the case of the endotoxin, to thereby form a gel and hydrolyzes a synthetic substrate [cf. Morita et al., FEBS Lett., 129, 318–321 (1981)].

Known examples of substances reacting with factor G include $(1 \to 3)$-$\beta$-D-glucan, krestin, lentinan and substances contained in rinses from cellulosic hemodialyzer and blood contacted therewith. It has been confirmed that none of these substances would show any positive reaction in a rabbit pyrogenic test.

Endotoxin is also known as cell wall components of gram-negative bacteria. Thus, the presence of gram-negative bacteria in vivo can be detected by determining endotoxin in blood. Accordingly, it has been urgently required in the field of clinical diagnosis to establish a method of assaying an endotoxin at a high sensitivity and a high reproducibility without being affected by $(1 \to 3)$-$\beta$-D-glucan.

Obayashi et al. reported a method of assaying an endotoxin by using factor C-system in the lysate [cf. Clin. Chim. Acta, 149, 55–65 (1985)]. However, this method requires a highly complicated procedure since it comprises fractionating the lysate by gel filtration or affinity chromatography with the use of a heparin or dextran sulfate-immobilized carrier, eliminating factor G sensitive to $(1 \to 3)$-$\beta$-D-glucan and thus reconstituting the lysate with factors C and B and the proclotting enzyme.

DESCRIPTION OF THE INVENTION

The present invention relates to a reagent for assaying an endotoxin through a reaction of factors C and B in lysate by using an antibody to the $(1 \to 3)$-$\beta$-D-glucan-sensitive factor so as to eliminate any effects of factor G sensitive to $(1 \to 3)$-$\beta$-D-glucan.

Namely, the reagent for assaying an endotoxin of the present invention includes:

(1) a reagent for assaying an endotoxin which comprises the lysate and an antibody to $(1 \to 3)$-$\beta$-D-glucan-sensitive factor; and (2) a reagent for assaying an endotoxin which comprises a lysate substantially free from any $(1 \to 3)$-$\beta$-D-glucan-sensitive factor obtained by contacting the lysate with a carrier on which an antibody to the $(1 \to 3)$-$\beta$-D-glucan-sensitive factor is immobilized.

As described above, the $(1 \to 3)$-$\beta$-D-glucan-sensitive factor is factor G activated by $(1 \to 3)$-$\beta$-D-glucan. The effects of factor G contained in the lysate should be eliminated to specifically assay an endotoxin by using the lysate without being affected by $(1 \to 3)$-$\beta$-D-glucan. In order to solve this problem, an antibody to factor G is used together with the lysate or a lysate substantially free from any factor G obtained by using anti-factor G antibody-immobilized carrier.

The lysate used in the present invention may be obtained by collecting the hemolymph of horseshoe crab such as *Limulus polyphemus* in U.S.A., *Tachypleus gigas* in Thailand and Malaysia, *Tachypleus tridentatus* in Japan and China, *CarcinoscorDius rotundicauda* in Thailand and Malaysia, grinding the blood cells and separating the component (lysate). It is preferable that the lysate is stored at −40° C. or below in small portions and thawed and dissolved upon use.

In order to produce an antibody to factor G from the lysate thus obtained, it is first required to purify factor G which serves as an antigen. Factor G may be purified by contacting the lysate with an appropriate carrier such as agarose, Sepharose (trade name of a product commercially available from Pharmacia), crosslinked derivatives thereof, on which dextran sulfate or heparin is immobilized, and then collecting fractions containing factor G. These processes may be conducted by, for example, contacting the above-described immobilized carrier with the lysate in a solution or by utilizing a column chromatography.

An antibody to $(1 \to 3)$-$\beta$-D-glucan-sensitive factor is produced by using as an antigen the purified factor G sensitive to $(1 \to 3)$-$\beta$-D-glucan or the factor G fraction free from factors C and B. Thus, polyclonal and monoclonal antibodies to these antigens are obtained.

The polyclonal antibody used in the present invention may be produced by administering the above-mentioned antigen to an animal to be immunized (for example, rabbit, goat). It is preferable to further purify the antibody thus obtained. When the antigen is administered to the animal, it is recommended to use an adjuvant since the antibody-producing cells can be activated thereby.

The monoclonal antibody used in the present invention may be produced by, for example, the following method. Namely, the above-mentioned antigen is intraperitoneally administered to a rat or a mouse and then the spleen of the animal is taken out. Cells collected from this spleen are fused with myeloma cells which are cells of tumor cell line to obtain hybridomas. After continuously proliferating these hybridomas in vitro, a cell line capable of continuously producing a specific antibody to the above-mentioned antigen is selected. Then, the selected cells are incubated either in vitro or in vivo (for example, in the abdominal cavity of a mouse) to produce a large amount of the monoclonal antibody. In addition to the above-mentioned spleen cells, lymph node cells and lymphocytes in peripheral blood may be used in the cell fusion. Preferable as the myeloma cells are those derived from the same species as compared to those derived from a different species, since hybridomas which stably produces the antibody can be obtained.

The polyclonal and monoclonal antibody thus obtained may be purified by salting out with a neutral salt such as sodium sulfate and ammonium sulfate, a cold alcohol precipitation or selective fractional precipitation using polyethylene glycol or utilizing an isoelectric point, electrophoresis, adsorption and desorption using an ion exchanger such as DEAE- or CM-derivatives, or adsorbents such as protein A or hydroxyapatite, gel filtration and ultracentrifugation.

In the above method (1) of assaying an endotoxin, the antibody may be combined with a solution of the lysate and endotoxin by the following methods: a method comprising dissolving a freeze-dried lysate in distilled water or an appropriate buffer solution and adding thereto a solution of the antibody; a method comprising freeze-drying a mixture of the lysate and the required amount of a solution of the antibody and dissolving the freeze-dried preparation in a distilled water or an appropriate buffer solution; a method comprising dissolving a freeze-dried product of a mixture of the lysate and a synthetic substrate in an appropriate buffer solution and adding thereto a solution of the antibody; a method comprising freeze-drying a mixture of the lysate, a synthetic substrate and the required amount of a solution of the antibody and dissolving the freeze-dried preparation in distilled water or an appropriate buffer solution; and a method comprising adding the required amount of a solution of the antibody to a sample.

In the above method (2), on the other hand, the lysate free from any factor G may be obtained by contacting the lysate with the antibody-immobilized carrier, by the following methods: a method comprising contacting the lysate with the carrier and then removing the carrier by, for example, centrifugation or filtration; and a method comprising applying the lysate to a column packed with the carrier and then collecting the fraction which passes through the column.

Usable as the carriers are those prepared by covalently binding a hydroxyl group of an appropriate carrier such as Cellulofine (trade name of a product commercially available from Seikagaku Corporation) or Sepharose to an amino group of the antibody in a conventional manner. In addition to the ones cited above, cellulose, agarose, polyacrylamide, dextran and porous silica beads may be used as the carrier.

The antibody may be immobilized on the carrier by, for example, introducing an active group into the carrier and then binding the antibody thereto. For example, the carrier is epoxy-activated followed by formylation and then the antibody is bound thereto.

When the lysate is contacted with the immobilized carrier, the pH value may be controlled in such a manner that factor C contained in the lysate and coagulation factors relating to the reaction initiated by the endotoxin and factor C are not inactivated. The pH value may preferably range from 6 to 9. Similarly, the contact may be made at such a temperature that the coagulation factors are not inactivated. The temperature may usually range from 0° to 45° C., preferably from 0° to 10° C.

Examples of the biological samples for assaying an endotoxin by the method of the present invention include blood, plasma and serum as well as endogenous and exogenous exudates and excretes such as cerebrospinal fluid, ascites, articular fluid, pleural effusion, milk and urine. When plasma is used as a sample, for example, it should be separated by adding an anticoagulant such as heparin, EDTA and citric acid.

An endotoxin may be assayed using the assay reagent of the present invention by the following methods: a method comprising adding a synthetic substrate such as the above-mentioned chromogenic or fluorogenic substrate to the reaction mixture and then determining the amidolytic activity of the clotting enzyme; a gelation method comprising examining gel formation due to coagulation with the naked eye; a turbidimetric method comprising measuring turbidity accompanying the coagulation by using an appropriate optical system; a turbidimetric kinetic assay comprising measuring the time required for achieving a specific turbidity by using an appropriate optical system; and a method of measuring a change in viscosity accompanying the coagulation in terms of a change in resonant frequency using a quartz chemical analyzer.

It is the first characteristic of the reagent for assaying an endotoxin of the present invention, which contains an antibody for factor G, that it shows an excellent ability to specifically bind to factor G and a neutralizing effect, even in a small amount. It is the second characteristic of the same that the antibody is free from any serine protease inhibitors such as antitrypsin and antithrombin III known as inhibitors of the limulus reaction and thus never deteriorates factor C activity.

To further illustrate the present invention in greater detail, and not by way of limitation, the following Examples will be given.

BEST MODE FOR PRACTICING THE INVENTION

EXAMPLE 1

Production of Polyclonal Antibody to Factor G

One liter of limulus hemolymph was centrifuged at 4° C. at 1,500 rpm for 10 minutes. To approximately 50 g of the precipitate (amebocyte) thus obtained was added 250 ml of 0.02M Tris-HCl buffer (pH 8.0). The mixture was homogeneously ground in a homogenizer (Polytoron R PT10 (trade mark), manufactured by Kinematica Co.) followed by extraction and centrifuged in a refrigerated centrifuge (Tomy Seiko RD-20III) at 10,000 rpm for 30 minutes. The resulting precipitate was further extracted with 150 ml portions of the above-mentioned buffer twice. Thus, 550 ml of the lysate was finally obtained.

Figure 1:
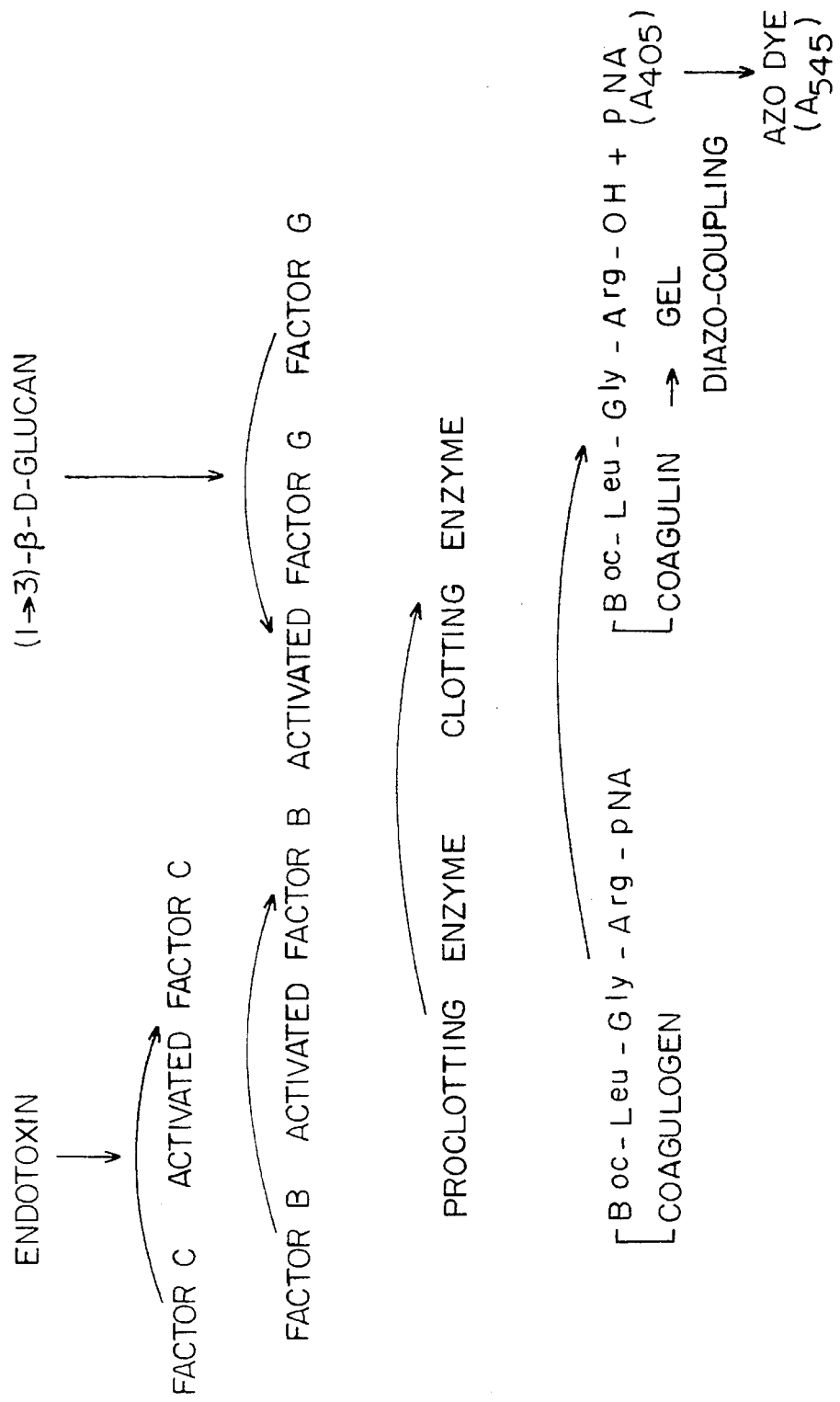
FIG. 1 shows the cascade mechanism of limulus blood coagulation system.

The whole lysate thus obtained was applied to a dextran sulfate-immobilized Sepharose CL-6B column [5×23 cm, equilibrated with 0.02M Tris-HCl buffer (pH 8.0) containing 0.05M NaCl] and eluted with a 0.02M Tris-HCl buffer (pH 8.0) containing 0.2M NaCl. The factor G fraction thus eluted, which contains factor G as shown in FIG. 1, was determined for G factor activity by the method of Obayashi et al. as described below [Clin. Chim. Acta, 149, 55–65 (1985)]. A 50 ml portion of the fraction was concentrated to 10 ml under reduced pressure and 0.23 g of EDTA-4Na was added thereto to inhibit the activation of factor G.

To 1.0 ml of the concentrate was added the equivalent amount of Freund's complete adjuvant (trade name of a product commercially available from Iatron Co.). Then, a rabbit (JW, male, 2.5 kg) was sensitized by subcutaneously injecting 0.3 ml, 0.3 ml and 0.4 ml portions of the mixture respectively at the back, hip and the side of the abdomen. The sensitization was effected once in 2 weeks (5 times in all). After confirming an increase in the antibody titer by the double immunodiffusion, the cervical vein was incised and the whole blood was collected one week after the final sensitization. The blood was allowed to stand at room temperature for 1 hour and then at 4° C. overnight. After centrifuging at 2,000 rpm for 5 minutes, 52 ml of the serum thus obtained was inactivated by heating at 56° C. for 30 minutes. To a 50 ml portion of the Serum was added 50 ml of a 34% (w/v) $Na_2SO_4$ solution and the precipitate thus formed was centrifuged at 10,000 rpm for 30 minutes. The resulting precipitate was washed with a 17% (w/v) $Na_2SO_4$ solution twice and the precipitate was dissolved in 50 ml of 0.1M Tris-HCl buffer (pH 8.0). 7.5 g of solid $Na_2SO_4$ was dissolved in this solution under stirring. The precipitate thus formed was dissolved in the same Tris-HCl buffer as used above. Further, the precipitation procedure was repeated thrice by using an $Na_2SO_4$ solution at a concentration of 7.5 g/50 ml and the precipitate thus finally obtained was dissolved in the above-mentioned buffer solution. Subsequently, it was desalted by passing through a Cellulofine GH-20m (trade name of a product commercially available from Seikagaku Corporation) column (2.8×90 cm, eluted with 0.05M $NH_4HCO_3$) equilibrated with 0.05M $NH_4HCO_3$. The eluate was freeze-dried, to obtain an IgG fraction of rabbit anti-factor G fraction serum.

Assay of Factor G Activity

To 0.1 ml of a 0.2M Tris-HCl buffer (pH 8.0, containing 0.013M $MgCl_2$) were added 0.03 ml of (1 → 3)-β-D-glucan (curdian, trade name of a product commercially available from Wako Pure Chemicals Industries, Ltd.; 400 ng/ml), 0.05 mi of each fraction, 0.02 ml of 0.005M N-tert-butoxycarbonyl(Boc)-Leu-Gly-Arg-p-nitroanilide (pNA) and 0.05 ml of proclotting enzyme and the mixture was allowed to react at 37° C. After confirming coloration, the reaction was stopped by adding 0.8 ml of 0.6M acetic acid. Then, the absorbance at 405 nm was measured.

EXAMPLE 2

Production of Polyclonal Antibody to Purified Factor G 1.2 liter of limulus hemolymph was centrifuged at 4° C. at 1,500 rpm for 10 minutes. To approximately 53 g of the precipitate (amebocyte) thus obtained was added 250 ml of 0.02M Tris-HCl buffer (pH 8.0, containing 0.001M benzamidine and 0.001M EDTA-4Na). The mixture was homogeneously ground, extracted and centrifuged at 10,000 rpm for 30 minutes in the same manner as in Example 1. The resulting precipitate was further extracted with 200 ml portions of the above-mentioned buffer twice. Thus, 640 ml of the lysate was finally obtained.

The whole lysate thus obtained was applied to a dextran sulfate-immobilized Sepharose CL-6B column [5×23.5 cm, equilibrated with 0.02M Tris-HCl buffer (pH 8.0)] and eluted with a 0.02M Tris-HCl buffer (pH 8.0) containing 0.2M NaCl. The factor G fraction thus eluted was applied to a Columnlite (trade name of product commercially available from Seikagaku Corporation) column [3.0×29.6 cm, equilibrated with 0.02M Tris-HCl buffer (pH 8.0)] and washed with 800 ml portions of a 0.02M Tris-HCl buffer (pH 8.0) and 0.5M $NH_4HCO_3$. After eluting with 2M $NH_4HCO_3$, purified factor G was obtained.

50 ml of the above-mentioned purified factor G solution was concentrated to 10 ml and then 0.23 g of EDTA-4Na was added thereto so as to inhibit the activation of factor G.

To 1.0 ml of the concentrate was added the equivalent amount of Freund's complete adjuvant. Then, a rabbit (JW, male, 2.5 kg) was sensitized by subcutaneously injecting 0.3 ml, 0.3 ml and 0.4 ml portions of the mixture respectively at the back, hip and the side of the abdomen. The sensitization was effected once in 2 weeks (5 times in all). After confirming an increase in the antibody titer by the double immunodiffusion, the cervical vein was incised and the whole blood was collected one week after the final sensitization. The blood was allowed to stand at room temperature for 1 hour and then at 4° C. overnight. After centrifuging at 2,000 rpm for 5 minutes, 65 ml of the serum thus obtained was inactivated by heating at 56° C. for 30 minutes. To 50 ml of this serum was added 50 ml of a 34% (w/v) $Na_2SO_4$ solution and the precipitate thus formed was centrifuged at 10,000 rpm for 30 minutes. The resulting precipitate was washed with a 17% (w/v) $Na_2SO_4$ solution twice and the precipitate was dissolved in 50 ml of 0.1M Tris-HCl buffer (pH 8.0). 7.5 g of solid $Na_2SO_4$ was dissolved in this solution under stirring. The precipitate thus formed was dissolved in the same Tris-HCl buffer as used above. Further, the precipitation procedure was repeated thrice by using $Na_2SO_4$ in a concentration of 7.5 g/50 ml and the precipitate thus finally obtained was dissolved in the above-mentioned buffer. Subsequently, it was desalted by passing through a Cellulofine GH-20m column (2.8×90 cm, eluted with 0.05M $NH_4HCO_3$) equilibrated with 0.05M $NH_4HCO_3$. The elute was freeze-dried to obtain an IgG fraction of anti-factor G serum.

EXAMPLE 3

Production of Monoclonal Antibody to Purified Factor G 0.5 ml (200 µg protein/ml) of factor G obtained in Example 2 was mixed with the equivalent amount of Freund's complete adjuvant. Then, the resulting mixture was subcutaneously injected into the back (0.2 ml) and the hip (0.3 ml) of a mouse (BALB/c, aged 5 weeks, 25 g body weight). The second sensitization was made two weeks after the first sensitization and the final immunization was made by intravenously administering 0.3 ml of 300 µg/ml factor G three weeks after the first sensitization. Four days thereafter, $9.2 \times 10^7$ spleen cells were separated and allowed to fuse with $1.8 \times 10^7$ mouse myeloma SP/O cells in a conventional manner to thereby give hybridomas. It was confirmed that the resulting hybridomas would bind to factor G and neutralize factor G activity. Next, 0.2 ml of pristan (2,6,10,14-tetramethylpentadecane) was intraperitoneally administered to a similar mouse as used above. After 1 week, $3 \times 10^7$ cells/mouse of the hybridomas were intraperitoneally administered to the mouse. In the second week, a large amount of ascites was pooled. The ascites was then collected and the IgG fraction was precipitated with 40%-saturated ammonium sulfate. Thus, an ascitic form monoclonal antibody was finally obtained.

EXAMPLE 4

Preparation of Factor G-free Lysate by Using Anti-factor G Antibody-immobilized Cellulofine 100 ml of the lysate obtained by the method described in Example 1 was applied to an endotoxin and β-glucan-free anti-factor G antibody-immobilized Cellulofine column (1.2×11 cm), which had been equilibrated with a 0.1M Tris-HCl buffer (pH 8.0, containing 0.15M NaCl), prepared by a method as described below and washed with a 0.1M Tris-HCl buffer (pH 8.0, containing 1M NaCl). Then the nonadsorbed fractions passed through the column were collected to obtain a factor G-free lysate containing substantially no factor G.

Preparation of Anti-factor G Antibody-immobilized Cellulofine 10 g of formylcellulofine was sufficiently washed with a 0.1M sodium phosphate buffer (pH 7.1) and suspended in 20 ml of a solution of each antibody to the respective factors G obtained in Examples 1 to 3 (10 mg/ml 0.1M sodium phosphate buffer, pH 7.1). Then, 50 mg of NaCNBH$_3$ was added thereto to obtain a suspension. After slowly stirring at room temperature for 8 hours, it was washed with a 0.2M Tris-HCl buffer (pH 7.0) and filtered. Subsequently, 5 ml of the above-mentioned buffer containing 10 mg of NaCNBH$_3$ was added thereto followed by shaking at room temperature for 3 hours. Then, it was sufficiently washed with a 0.1M Tris-HCl buffer (pH 8.0, containing 0.15M NaCl).

EXAMPLE 5

Assay of Endotoxin

Three reagents were produced by the following methods and their reactivities with 3 samples were examined for comparison.

The reagent A was produced by mixing 440 µl of the lysate, 440 µmol of magnesium chloride and 2.86 µmol of Boc-Leu-Gly-Arg-pNA followed by freeze-drying. The agent B was produced by adding 180 µl of a 10 mg/ml solution of the IgG fraction of the anti-factor G fraction serum produced in Example 1 in a 0.02M Tris-HCl buffer (pH 8.0) to the components of the reagent A followed by freeze-drying. The reagent C was produced by adding 180 µl of a 10 mg/ml solution of the IgG fraction of the anti-factor G serum produced in Example 2 in a 0.02M Tris-HCl buffer (pH 8.0) to the components of the reagent A followed by freeze-drying.

These three reagents were each dissolved in 2.2 ml of a 0.2M Tris-HCl buffer (pH 8.0) and 0.1 ml portions of the resulting solution were pipetted into test tubes. 0.1 ml of a sample was added thereto and mixed well. The mixture was allowed to react at 37° C. for 30 minutes. The reactivities of the three reagents with the samples were examined by inducing the coloration of the pNA formed after 30 minutes by successively adding 0.5 ml of 0.04% sodium nitrite (in 0.48M hydrochloric acid), 0.3% ammonium sulfamate and 0.07% N-(1-naphthyl)ethylenediamine dihydrochloride and measuring the absorbance at 545 nm. Table 1 shows the results. As these results clearly show, the endotoxin can be specifically assayed by using a reagent, which includes a polyclonal antibody to the factor G fraction and a polyclonal antibody to factor G, without being affected by (1 → 3)-β-D-glucan.

TABLE 1

| Sample (pg/tube) | | Reactivity (ΔA545 nm/30 min) | | |
|---|---|---|---|---|
| Endotoxin* | Glucan** | Reagent A no antibody | Reagent B factor G fraction antibody | Reagent C factor G antibody |
| | 3.0 | 0.242 | 0.001 | 0.001 |
| 2.5 | | 0.447 | 0.445 | 0.448 |
| 2.5 | 3.0 | 0.691 | 0.447 | 0.446 |

*: Derived from *E. coli* 0111:B4.
**: Curdlan.

EXAMPLE 6

Assay of Endotoxin

Two reagents were produced by the following methods and their reactivities with an endotoxin and (1 → 3)-β-D-glucan were and examined for comparison.

The reagent A was produced by mixing 440 µl of the lysate, 440 µmol of magnesium chloride and 2.86 µmol of Boc-Leu-Gly-Arg-pNA followed by freeze-drying. The reagent D was produced by adding 80 µl of a solution containing the monoclonal antibody capable of neutralizing the purified factor G prepared in Example 3 to the components of the reagent A followed by freeze-drying.

These two reagents were each dissolved in 2.2 ml of a 0.2M Tris-HCl buffer (pH 8.0) and 0.1 ml portions of the resulting solution were pipetted into test tubes. 0.1 ml of a sample was added thereto and mixed well. The mixture was allowed to react at 37° C. for 30 minutes. The reactivities of the two reagents with the samples were examined by inducing the coloration of the pNA formed after 30 minutes by successively adding 0.5 ml of 0.04% sodium nitrite (in 0.48M hydrochloric acid), 0.3% ammonium sulfamate and 0.07% N-(1-naphthyl)ethylenediamine dihydrochloride and measuring the absorbance at 545 nm.

Figure 2:
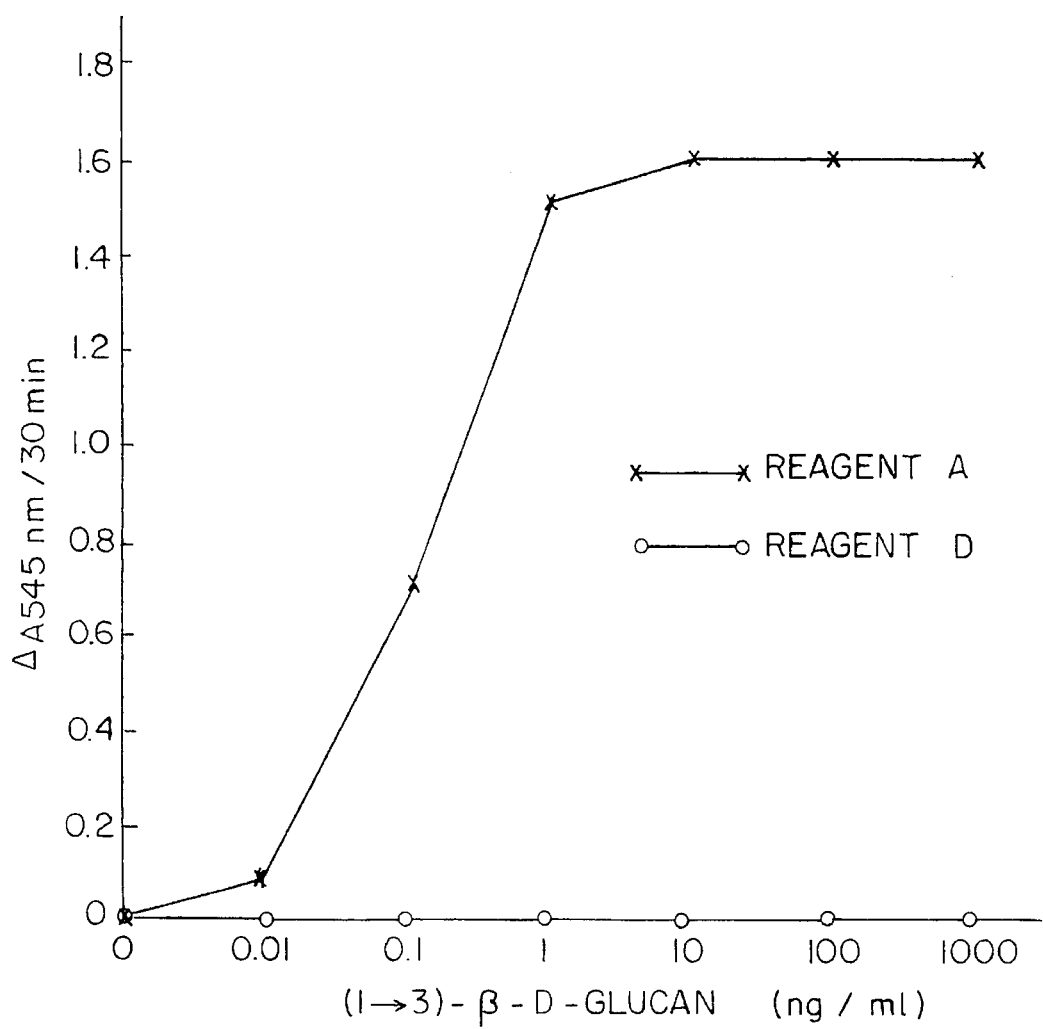
FIG. 2 shows the reactivities of reagents A and D against $(1 \rightarrow 3)$-$\beta$-D-glucan.

FIG. 2 shows the results of the comparison of the reactivity of the reagents with (1 → 3)-β-D-glucan. The reagent A reacted with the (1 → 3)-β-D-glucan depending on concentration, while the reagent D never reacted with (1 → 3)-β-D-glucan of 1,000 ng/ml. These results indicate that the monoclonal antibody to the purified factor G had completely neutralized factor G in the lysate and thus its reactivity with (1 → 3)-β-D-glucan had been eliminated.

Figure 3:
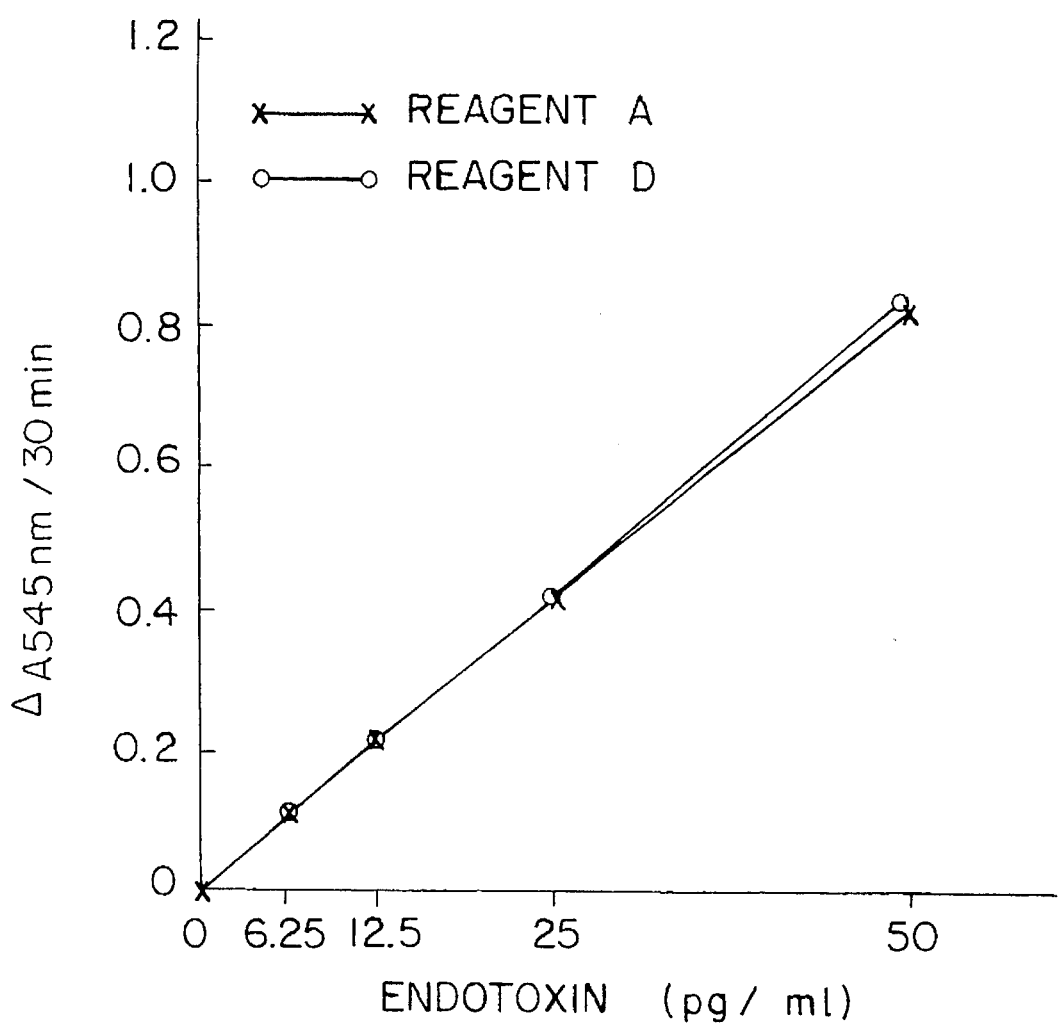
FIG. 3 shows the reactivities of the reagents A and D against *E. coli* 0111:B4 endotoxin.

FIG. 3 shows the comparison of the reactivities of the reagents A and D with the endotoxin with the use of the dose-response curves of these reagents. As FIG. 2 shows, the dose-response curves of these reagents almost agree with each other. This fact means that the monoclonal antibody to factor G in the reagent D never affected the reactivity of the lysate with endotoxin.

Figure 4:
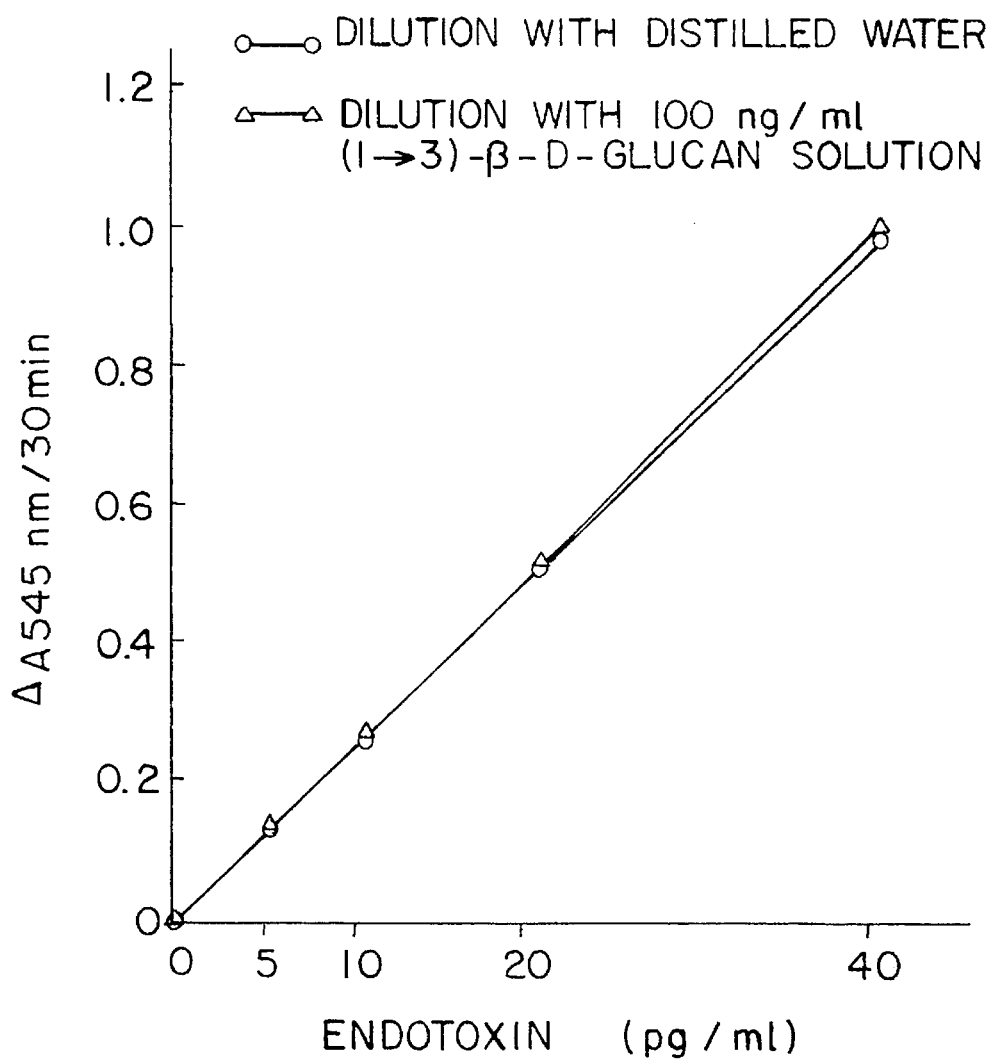
FIG. 4 shows the reactivities of the reagent D against *Salmonella enteritidis* endotoxin diluted with water and a solution containing $(1 \rightarrow 3)$-$\beta$-D-glucan.

FIG. 4 shows the dose-response curves of the reagent D against a serial dilution of the endotoxin with distilled water and another serial dilution thereof with a 100 ng/ml (1 → 3)-β-D-glucan solution. These two dose-response curves almost agree with each other, which means that the endotoxin can be specifically assayed, without being affected by (1 → 3)-β-D-glucan contained in a sample, by using the agent D.

These results clearly indicate that an endotoxin can be specifically assayed, without being affected by (1 → 3)-β-D-glucan, by using a reagent including a monoclonal antibody to the purified factor G.

EXAMPLE 7

Assay of Endotoxin

Two reagents were produced by the following methods and their reactivities with 3 samples were examined for comparison.

The reagent A was produced by mixing 440 μl of the lysate, 440 μmol of magnesium chloride and 2.86 μmol of Boc-Leu-Gly-Arg-pNA followed by freeze-drying. The reagent E was produced by mixing 440 μl of the factor G-free lysate produced in Example 4 with 2.86 μmol of Boc-Leu-Gly-Arg-pNA, followed by freeze-drying.

These two reagents were each dissolved in 2.2 ml of a 0.2M Tris-HCl buffer (pH 8.0) and 0.1 ml portions of the resulting solution were pipetted into test tubes. 0.1 ml of a sample was added thereto and mixed well. The mixture was allowed to react at 37° C. for 30 minutes. The reactivities of the two reagents with the samples were examined by inducing coloration of the pNA formed after 30 minutes by successively adding 0.5 ml of 0.04% sodium nitrite (in 0.48M hydrochloric acid), 0.3% ammonium sulfamate and 0.07% N-(1-naphthyl)ethylenediamine dihydrochloride and measuring the absorbance at 545 nm. Table 2 summarizes the results. As these results clearly show, the endotoxin can be specifically assayed by using a reagent, which has been produced by using the aforesaid factor G-free lysate, without being affected by (1 → 3)-β-D-glucan.

TABLE 2

| Sample (pg/tube) | | Reactivity (ΔA545 nm/30 min) | |
|---|---|---|---|
| Endotoxin* | Glucan** | Reagent A lysate | Reagent E factor G-free lysate |
|  | 3.0 | 0.227 | 0.001 |
| 2.5 |  | 0.439 | 0.437 |
| 2.5 | 3.0 | 0.668 | 0.439 |

*: Derived from *E. coli* 0111:B4.
**: Curdlan.

EXAMPLE 8

Assay of Plasma Specimen

Subjects were 25 patients being in the hospital of the Department of Hematology attached to Jichi Medical School, who suffered from hepatic and bile duct diseases accompanied by serious hemopathy such as leukemia and infection and further seemed to suffer from septicaemia due to gram-negative bacteria. Blood was aseptically collected from each subject followed by adding heparin to serve as a sample. The heparin-added blood samples were centrifuged at 4° C. at 150×G for 10 minutes to give platelet rich plasma (PRP) samples. To 0.1 ml of each PRP sample was added 0.2 ml of 0.32M perchloric acid and the mixture was incubated at 37° C. for 20 minutes. The precipitate was removed by centrifugation at 3,000 rpm for 10 minutes. 0.05 ml of the resulting supernatant was neutralized with 0.05 ml of 0.18M NaOH. Thus a specimen was obtained.

Figure 5:
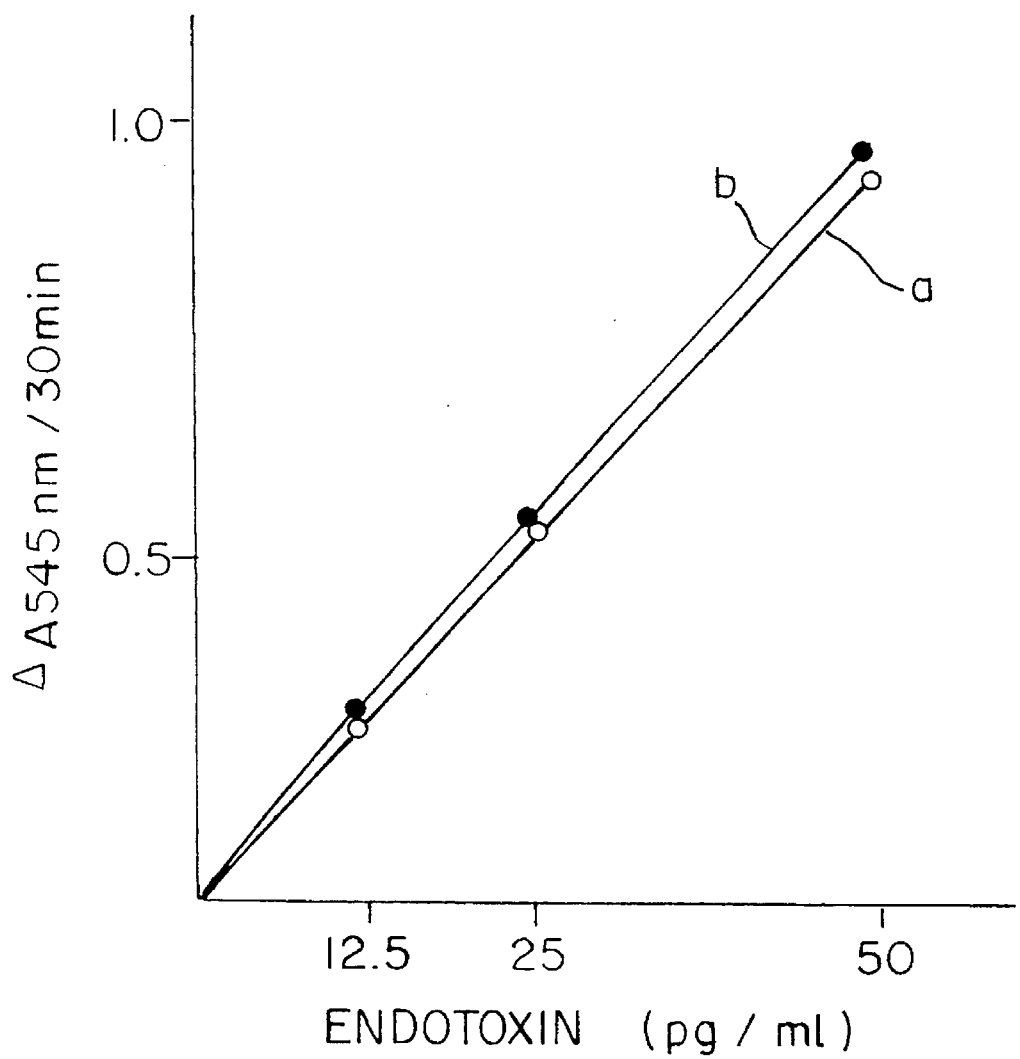
FIG. 5 shows calibration curves of *E. coli* 0111:B4 endotoxin prepared in Examples 8 to 10.
Figure 6:
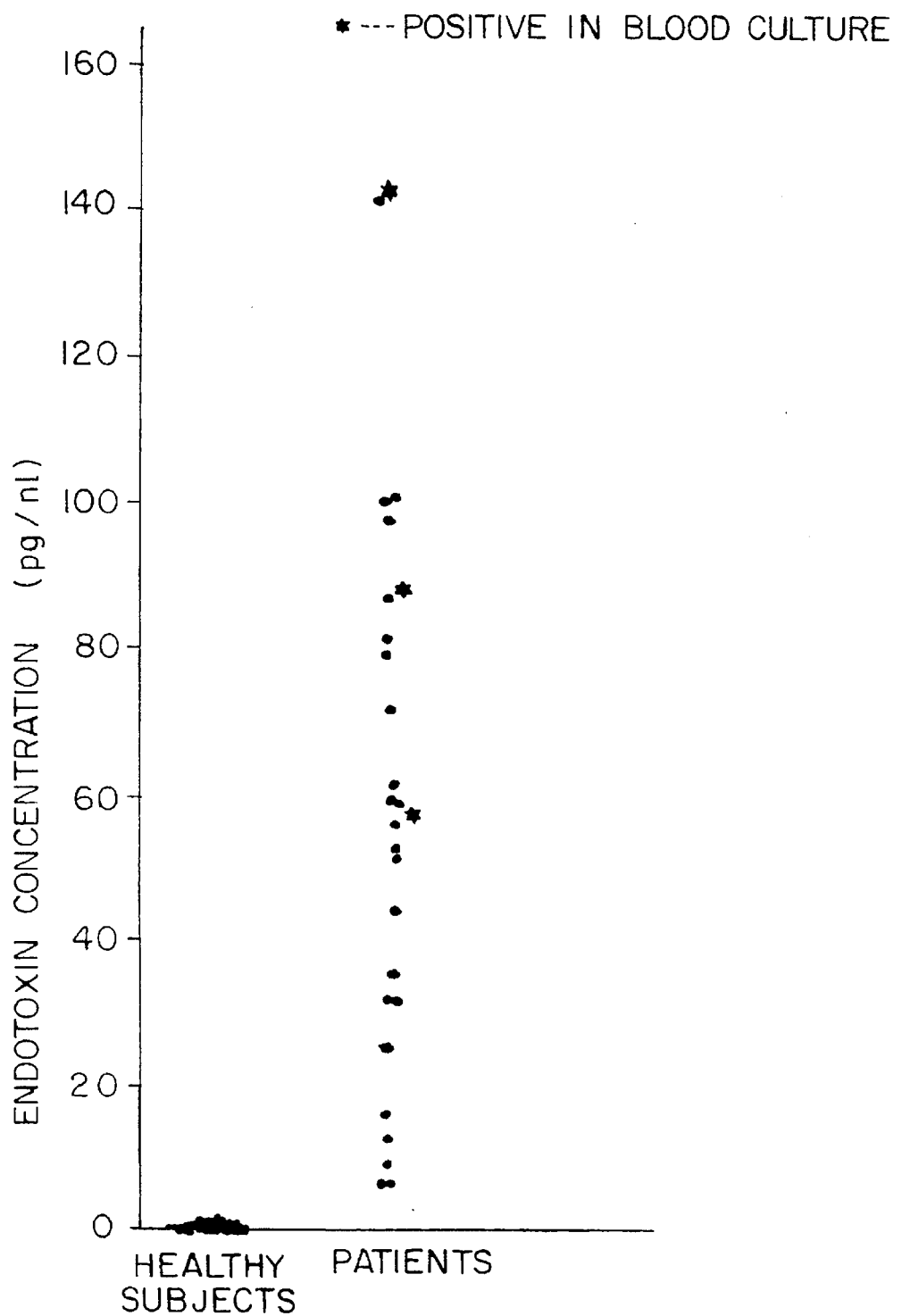
FIG. 6 shows the results of the assay of endotoxin contained in plasma specimens in Example 8.

Next, 0.1 ml of the endotoxin assay reagent of the present invention produced by the method described in Example 6 was added thereto and the mixture was incubated at 37° C. for 30 minutes. To the resulting solution, 0.5 ml portions of 0.04% sodium nitrite (in 0.48M hydrochloric acid), 0.3% ammonium sulfamate and 0.07% N-(1-naphthyl)ethylenediamine dihydrochloride were successively added to thereby perform diazo-coupling. Then, the absorbance of the resulting mixture was measured at 545 nm. The level of the *E. coli* 0111:B4 endotoxin was calculated from the calibration curve a (FIG. 5) which had been separately prepared. As FIG. 6 shows, the endotoxin was detected at high concentrations in all of the 25 samples (healthy 25 subjects: 0.8±0.6 pg/ml). Further, *Escherichia coli*, *Pseudomonas aeruginosa* and *Klebsiella pneumoniae* were respectively detected from 3 (*) out of 25 samples by blood culture. Although the remaining 22 samples showed negative results in blood culture, they were diagnosed as gram-negative bacterial septicaemia based on clinical symptoms including fever and leukocyte count as well as sensitivities for antibiotics. Thus, it can be understood that the method of the present invention is highly useful in rapidly diagnosing gram-negative bacterial septicaemia which can be hardly diagnosed by known test methods.

EXAMPLE 9

Assay of Urine Specimen

The endotoxin was assayed according to the method of the present invention for the urine of 3 patients suffering from complicated urinary tract infection while being in the hospital attached to Jichi Medical School, in which *Escherichia coli* and *Serratia marcescens* had been detected by urine culture.

The intermediate urine of each subject was aseptically collected in a sterilized cup. To 0.005 ml of this urine was added 0.2 ml of the endotoxin assay reagent of the present invention produced by the method described in Example 7 and the resulting mixture was incubated at 37° C. for 30 minutes. After performing diazo-coupling in the same manner as in Example 8, the absorbance of the solution was determined at 545 nm. The level of *E. coli* 0111:B4 endotoxin was calculated from the calibration curve b (FIG. 5) which had been separately prepared. As Table 3 shows, the endotoxin was detected at high concentrations in all of the samples (healthy subjects: 60 pg/ml or less). Thus, it can be understood that the method of the present invention is highly useful in rapidly diagnosing gram-negative bacterial urinary tract infection.

TABLE 3

Endotoxin concentration in urine of subjects suffering from gram-negative bacterial infection

| No. | Detected bacterium | CFU*/ml | Endotoxin (ng/ml) |
|---|---|---|---|
| 1 | Escherichia coli | >$10^5$ | 1056.5 |
| 2 | Serratia marcescens | >$10^3$ | 18.0 |
| 3 | Serratia marcescens | >$10^4$ | 216.7 |

*: Colony-forming unit.

EXAMPLE 10

Assay of Cerebrospinal Fluid Specimen

The endotoxin was determined by the method of the present invention for cerebrospinal fluid samples collected from 3 subjects who had seemed to suffer from meningitis in the hospital attached to Jichi Medical School, from which *Pseudomonas aeruginosa* and *Haemophilus influenzae* had been detected.

0.05 ml of distilled water for injection was added to 0.05 ml of the cerebrospinal fluid of each subject aseptically collected by lumbar puncture. Further, 0.1 ml of the endotoxin assay reagent of the present invention produced by the method described in Example 5 was added thereto and the resulting mixture was incubated at 37° C. for 30 minutes. After performing diazo-coupling in the same manner as in Example 8, the absorbance of the solution was determined at 545 nm. The level of the *E. coli* 0111:B4 endotoxin was calculated from the calibration curve b (FIG. 5) which had been separately prepared. As Table 4 shows, the endotoxin was detected at high concentrations in all of the 3 samples (healthy subjects: 3 pg/ml or less). Thus, it can be understood that the method of the present invention is highly useful in rapidly diagnosing gram-negative bacterial meningitis in the early stage.

TABLE 4

Endotoxin concentration in cerebrospinal fluid of subject suffering from gram-negative bacterial infection

| No. | Detected bacterium | Endotoxin (pg/ml) |
|---|---|---|
| 1 | Pseudomonas aeruginosa | 75.5 |
| 2 | Pseudomonas aeruginosa | 108.5 |
| 3 | Haemophilus influenzae | 34.6 |

INDUSTRIAL APPLICABILITY

As described above, the present invention provides a reagent comprising the lysate for specifically assaying an endotoxin whereby an endotoxin originating from gram-negative bacteria contained in biological samples (for example, blood, urine, cerebrospinal fluid) can be rapidly and easily assayed at a high accuracy. Therefore, the assay reagent of the present invention is useful in rapidly diagnosing gram-negative bacterial septicaemia and endotoxemia and evaluating therapeutic effects on these diseases. Thus, it greatly contributes to, in particular, clinical diagnosis.

Furthermore, the present invention makes it possible to rapidly and accurately assay an endotoxin contaminating distilled water for injection, medical devices and injections, such a secondary effect according to the present invention greatly contributes to the field of the drug manufacturing industries.

What is claimed is:

1. A reagent for assaying an endotoxin comprising limulus amebocyte lysate and an antibody to $(1 \rightarrow 3)$-β-D-glucan sensitive factor, wherein said antibody specifically binds to and neutralizes $(1 \rightarrow 3)$-β-D-glucan sensitive factor.

2. The reagent for assaying an endotoxin as claimed in claim 1, wherein said antibody is a monoclonal antibody.

3. The reagent for assaying an endotoxin as claimed in claim 1, wherein said antibody is a polyclonal antibody.

4. A reagent for assaying an endotoxin comprising limulus amebocyte lysate, an antibody to $(1 \rightarrow 3)$-β-D-glucan sensitive factor, wherein said antibody specifically binds to and neutralizes $(1 \rightarrow 3)$-β-D-glucan sensitive factor, and a synthetic peptide substrate for clotting enzyme having an amino acid sequence in common with the hydrolysis sites of coagulogen.

5. The reagent for assaying an endotoxin as claimed in claim 4, wherein said antibody is a monoclonal antibody.

6. The reagent for assaying an endotoxin as claimed in claim 4, wherein said antibody is a polyclonal antibody.

7. A reagent for assaying an endotoxin comprising a limulus amebocyte lysate substantially free from $(1 \rightarrow 3)$-β-D-glucan sensitive factor, obtained by method (I) or (II), wherein said method (I) comprises the steps of:

(a) admixing limulus amebocyte lysate with a carrier onto which an antibody to $(1 \rightarrow 3)$-β-D-glucan sensitive factor has been immobilized, wherein said antibody specifically binds to and neutralizes $(1 \rightarrow 3)$-β-D-glucan sensitive factor, and (b) removing the carrier from the lysate so as to obtain said reagent;

wherein said method (II) comprises the steps of:

(a) applying limulus amebocyte lysate to a column which has previously been packed with a carrier onto which an antibody to $(1 \rightarrow 3)$-β-D-glucan sensitive factor has been immobilized, wherein said antibody specifically binds to and neutralizes $(1 \rightarrow 3)$-β-D-glucan sensitive factor, and (b) collecting a fraction of the lysate which passes through the column so as to obtain said reagent.

8. The reagent for assaying an endotoxin as claimed in any one of claims 1 to 7, wherein said reagent is a freeze-dried preparation.

9. The reagent for assaying an endotoxin as claimed in claim 7, wherein said carrier onto which the antibody is immobilized is selected from the group consisting of cellulose, agarose, polyacrylamide, dextran and porous silica beads.

10. A method of assaying for an endotoxin in a sample comprising:

(a) combining the reagent of claim 7 with a sample under conditions whereby endotoxin in the sample, acting via an endotoxin-sensitive factor-dependent cascade, activates clotting enzyme in the reagent, (b) contacting the activated clotting enzyme with a synthetic peptide substrate for clotting enzyme having an amino acid sequence in common with the hydrolysis sites of coagulogen, and (c) measuring enzymatic activity of the activated clotting enzyme on coagulogen or on the synthetic peptide substrate as an indication of endotoxin in the sample.

11. A method of assaying for an endotoxin in a sample comprising:

(a) admixing limulus amebocyte lysate with an antibody to (1 → 3)-β-D-glucan sensitive factor, wherein said antibody specifically binds to and neutralizes (1 → 3)-β-D-glucan sensitive factor in the lysate, (b) combining the admixed lysate with a sample under conditions whereby endotoxin in the sample, acting via an endotoxin-sensitive factor-dependent cascade, activates clotting enzyme in the lysate, (c) contacting the activated clotting enzyme with a synthetic peptide substrate for clotting enzyme having an amino acid sequence in common with the hydrolysis sites of coagulogen, and (d) measuring enzymatic activity of the activated clotting enzyme on coagulogen or on the synthetic peptide substrate as an indication of endotoxin in the sample.

* * * * *